United States Patent [19]

Itoh et al.

[11] Patent Number: 5,026,733

[45] Date of Patent: Jun. 25, 1991

[54] BRAIN FUNCTION-IMPROVING MEDICINE

[75] Inventors: Kouichi Itoh; Atsushi Ishige; Eikichi Hosoya, all of Ibaraki, Japan

[73] Assignee: Tsumura & Co., Tokyo, Japan

[21] Appl. No.: 439,393

[22] PCT Filed: Mar. 17, 1989

[86] PCT No.: PCT/JP89/00290

§ 371 Date: Nov. 17, 1989

§ 102(e) Date: Nov. 17, 1989

[87] PCT Pub. No.: WO89/08451

PCT Pub. Date: Sep. 21, 1989

[30] Foreign Application Priority Data

Mar. 17, 1988 [JP] Japan .................................. 63-61871
Sep. 16, 1988 [JP] Japan ................................ 63-230142

[51] Int. Cl.$^5$ ............................................. A01N 31/14
[52] U.S. Cl. ..................................... 514/718; 514/721
[58] Field of Search ................................ 514/718, 721

Primary Examiner—Stanley J. Friedman
Assistant Examiner—Theodore I. Craires
Attorney, Agent, or Firm—Burns, Doane, Swecker & Mathis

[57] ABSTRACT

A brain function-improving medicine comprising, as an effective ingredient, a compound represented by the following formula:

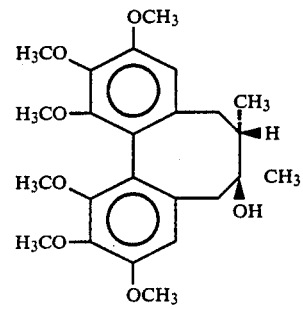

This medicine is effectively used for curing a disease caused by reduction of the central acetylcholinergic function.

5 Claims, No Drawings

BRAIN FUNCTION-IMPROVING MEDICINE

TECHNICAL FIELD

The present invention relates to a brain function-improving medicine.

BACKGROUND ART

Currently, the number of people more than 55 years old comprises more than 10% of the total population of this country, and thus it is considered that the number of patients suffering from dementia will greatly increase with the inevitable increase of the number of old people in the population, whereby serious problems will arise due to the increase in the number of patients suffering from dementia, the burden on families having to attend to such patients, and the necessity for an increase in the number of medical institutions.

Accordingly, the development of brain function-improving medicines such as psychotropic drugs and dementia-curing agents is urgently required.

As a medicine for remedy of schizophrenia, namely a psychotropic drug, Haloperidol, Chlorpromazine and Tetrabenazine are used.

These medicines, however, have adverse side effects such as a reduction of the learning function, and thus the administration of these medicines is limited, and therefore, a satisfactory medicinal effect cannot be obtained thereby.

DISCLOSURE OF THE INVENTION

The present inventors investigated various pharmacognostic components with a view to developing a medicine not showing an effect of reducing the learning function but exerting excellent psychotropic and anti-dementia effects, and as the result, found that a compound represented by the following formula:

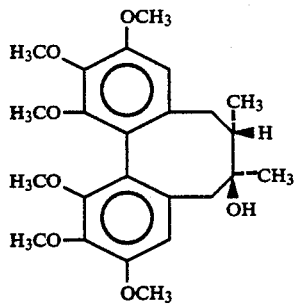

which is an extract component of the crude drug "Shizandra chinensis", has not only an excellent psychotropic action but also an excellent anti-dementia 1 action. The present invention was completed based on this finding.

More specifically, in accordance with the present invention, there is provided a brain function-improving medicine comprising a compound represented by the following formula (hereinafter referred to as "compound of the formula"):

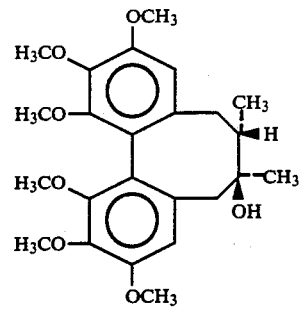

as an effective ingredient.

BEST MODE OF CARRYING OUT THE INVENTION

The compound of the formula can be obtained, for example, by the process disclosed in [Y. Ikeya, H. Taguchi, I. Yoshioka and H. Kobayashi, Chem. Pharm. Bull., 27(6), 1383 (1979)].

More specifically, "Shizandra chinensis" is extracted in a warm state with a lower hydrocarbon such as petroleum ether, n-hexane or benzene, the solvent is removed from the extract, and the residue is dissolved in water and subjected to steam distillation to remove an essential oil. The obtained non-essential-oil component is subjected to chromatography using a silica gel, and the development is carried out by using n-hexane, benzene, acetone or a mixture thereof to obtain the intended compound.

A specific example of the preparation of the compound of the formula will now be described.

SPECIFIC EXAMPLE

A product obtained by pulverizing 1.38 kg of "Shizandra chinensis" was refluxed and extracted with 3 l of petroleum ether, and this extraction was conducted four times. The extracts were combined, and the petroleum ether was removed under reduced pressure to obtain 188 g of a petroleum ether extract. This extract was suspended in 450 ml of water and the suspension was subjected to steam distillation for 3 hours to remove an essential oil. The residue was extracted with 200 ml of ether 4 times, the ether extracts were combined, and the ether was removed to obtain 179 g of a petroleum ether-soluble non-essential-oil portion (hereinafter referred to as "fraction A").

Then, "Shizandra chinensis" extracted with petroleum ether was extracted in a warm state with 3 l of methanol for 3 hours, and this extraction was conducted 3 times. The methanol extracts were combined and the mixture was concentrated to obtain 383 g of a methanol extract. This extract was dissolved in 580 ml of water and the solution was subjected to shaking extraction with 850 ml of ethyl acetate 3 times. The ethyl acetate extracts were combined and concentrated under reduced pressure to obtain 78 g of an extract. The extract was dissolved in methanol and 300 g of Celite 535 (supplied by Johns-Manville Co.) was sprinkled with the solution, and column chromatography was carried out and the development was conducted with 2 l of n-hexane. The eluate was concentrated under reduced pressure to obtain 20.8 g of an extract (hereinafter referred to as "extract B").

Then, the fraction A (179 g) was combined with the fraction B (20.8 g) and the mixture was subjected to column chromatography using 1200 g of a silica gel. The eluates with benzene/acetone (7/3) and benzene/acetone (3/2) were combined and concentrated to obtain 8.3 g of a residue. The residue was subjected to the column chromatography using 180 g of a silica gel and developed with an n-hexane/acetone mixed solvent. The eluate with n-hexane/acetone (22/3) was crystallized by n-hexane/ether to obtain 3.5 g of the compound of the formula (the yield was 0.25%).

With reference to the following test examples, it will now be explained that the compound of the formula has no action of reducing the learning function but shows psychotropic and anti-dementia actions.

TEST EXAMPLE 1

A male ICR strain mouse (5-weeks-old) was admitted in a bright chamber of a step-through passive avoidance learning device. After 60 seconds, a guillotine door was opened. Just after the mouse entered a dark room, the guillotine door was shut, and a foot shock of 0.15 mA was given to the mouse for 5 seconds. This operation was conducted until the mouse stayed in the bright room for more than 1 minute. Then, the mouse was taken out and 3 mg/kg of the compound of the formula was orally administered, and the mouse was returned to a home cage.

After 24 hours, the mouse was admitted into the bright chamber, and after 60 seconds, the guillotine door was opened and the time required for the mouse to enter in the dark room was measured as 300 seconds at longest. Furthermore, 3 mg/kg of the compound of the formula was orally administered, and the spontaneous movement quantity for 4 hours after the oral administration was measured by an animex and the total quantity was calculated. Note, 1% Tween was orally administered to the control group. The results are shown Table 1.

TABLE 1

| Control Group | Group to Which Compound of Formula Was Administered |
|---|---|
| A 229 ± 30.4 | >300 |
| B 5123 ± 259 | 6693 ± 474 |

Note
A: time (seconds) required for the mouse to enter dark room
B: sum of spontaneous movement quantity for 4 hours

TEST EXAMPLE 2

The compound of the formula (3 mg/kg) was orally administered to a male ICR strain mouse (5-weeks-old), and after 2 hours, 2 mg/kg of methamphethamine was intraperitoneally administered. The locomotor activity for every 15 minutes was measured by an animex, and the measurement was conducted for 120 minutes. To the control group, 1% Tween 80 was administered instead of the compound of the formula, and after 2 hours, 2 mg/kg of methamphethamine was intraperitoneally administered. The locomotor activity was similarly measured.

The results are shown in Table 2.

TABLE 2

| | Control Group | Group to which Compound of Formula Was Administered |
|---|---|---|
| after 15 minutes | 1250 ± 68 | 1034 ± 111 |
| after 30 minutes | 1551 ± 33 | 1295 ± 34 |
| after 45 minutes | 1511 ± 32 | 1245 ± 50 |
| after 60 minutes | 1429 ± 38 | 1156 ± 49 |

TABLE 2-continued

| | Control Group | Group to which Compound of Formula Was Administered |
|---|---|---|
| after 75 minutes | 1344 ± 34 | 1087 ± 40 |
| after 90 minutes | 1228 ± 44 | 989 ± 53 |
| after 120 minutes | 1126 ± 28 | 898 ± 60 |

From the results obtained in Test Examples 1 and 2, it was confirmed that the compound of the formula controls the locomotor activity by methamphethamine and a reduction of the avoidance learning function is not observed, and the compound of the formula has an excellent psychotropic action.

TEST EXAMPLE 3

In the same manner as described in Test Example 2, 3 mg/kg of the compound of the formula was orally administered to a male ICR strain mouse (6-weeks-old), and after 2 hours, 2 mg/kg of scopolamine was intraperitoneally administered. For 120 minutes from the point of the application, the locomotor activity was measured by an animex. To the control group, 1% Tween 80 was orally administered and 2 mg/kg of scopolamine was intraperitoneally administered, and the locomotor activity was similarly measured.

It was found that the locomotor activity was 6353±296 in the control group and the locomotor activity was 3991±389 in the group to which the compound of the formula was administered.

TEST EXAMPLE 4

The compound of the formula was orally administered to a male ICR strain mouse (9-weeks-old), and after 2 hours, 2 mg/kg of scopolamine was applied to the abdominal cavity. After 30 minutes, the mouse was irradiated with 10 KW of microwaves for 0.5 seconds, and the brain was extracted and then divided into two parts, that is, the cerebral cortex (inclusive of hippocampus) and the subcerebral part. The wet weights were measured and the acetylcholine (hereinafter referred to as "ACh") contents were measured according to the following method.

Each part of the brain was homogenized by 0.1N perchloric acid ($HClO_4$) and subjected to centrifugal separation under 30000 g for 15 minutes. The supernatant was passed through a 0.45 μm microfilter and poured into HPLC-ECD.

The measurement conditions were as follows.
Moving phase: phosphate buffer (pH 8.0)
Flow rate: 1 ml/min
Voltage: +450 mV
Full scale: 1.6 nA
Enzyme immobilized column: Eicom AC-Enzmpak
Anakyzing column: Eicom AC-ODS (4.6 mm in diameter and 250 mm in length)

The compound of the formula was orally administered while scopolamine was not applied, and after 2 hours and 30 minutes, the ACh content was determined in the same manner as described above.

The obtained results are shown in Tables 3 and 4.

TABLE 3

| Effect of ACh Content at Cerebral Cortex | | |
|---|---|---|
| Amount Administered (mg/kg) of Compound of Formula | Amount Administered (mg/kg) of Scopolamine | ACh Content (nM/g of wet weight) |
| 0 | 0 | 15.7 |

TABLE 3-continued

Effect of ACh Content at Cerebral Cortex

| Amount Administered (mg/kg) of Compound of Formula | Amount Administered (mg/kg) of Scopolamine | ACh Content (nM/g of wet weight) |
| --- | --- | --- |
| 3 | 0 | 20.9 |
| 30 | 0 | 21.7 |
| 0 | 2 | 11.4 |
| 3 | 2 | 13.9 |
| 30 | 2 | 13.7 |

TABLE 4

Effect of ACh Content at Subcerebral Part

| Amount Administered (mg/kg) of Compound of Formula | Amount Administered (mg/kg) of Scopolamine | ACh Content (nM/g of wet weight) |
| --- | --- | --- |
| 0 | 0 | 27.8 |
| 3 | 0 | 35.0 |
| 30 | 0 | 38.9 |
| 0 | 2 | 23.3 |
| 3 | 2 | 26.9 |
| 30 | 2 | 26.1 |

From the results obtained in Test Examples 3 and 4, it was confirmed that the compound of the formula controls the locomotor activity by scopolamine and increases the ACh contents at the cerebral cortex and the subcerebral part, and that this effect is obtained under the application of scopolamine.

From the foregoing experimental results, it was confirmed that the compound of the formula has an acetylcholinergic nerve-activating action and is valuable as a medicine for diseases caused by a reduction of the central acetylcholinergic function, such as Alzheimer's disease, Alzheimer type senile dementia, Huntington's chorea, and Pick's disease.

As apparent from the foregoing description, the compound of the formula is valuable as a brain function-improving medicine such as a psychotropic drug or anti-dementia medicine.

When the acute toxicity by the oral administration of the compound of the formula was tested by using male ddy strain mice and male wistar strain rats, it was found that $LD_{50}$ was 900 mg/kg.

The compound of the formula has a low toxicity and is very safe.

The administration dose and formulation of the compound of the formula will now be described.

The compound of the formula can be administered to humans and animals as it is or together with a pharmaceutical carrier.

The administration mode is not particularly critical and an appropriate administration mode is selected according to need. For example, there can be used oral medicines such as a tablet, a capsule, a granule, a fine granule and a powder, and non-oral medicines such as an injection and a suppository.

In the case of an oral medicine, to obtain the intended effect, preferably 5 to 500 mg of the compound of the formula is divided and administered several times to an adult in one day, although the preferred dose differs according to the age and body weight of a patient and the degree of the disease.

An oral medicine of the compound of the formula, such as a tablet, a capsule or a granule, is prepared according to customary procedures by using, for example, starch, lactose, white sugar, mannitol, carboxymethyl cellulose, corn starch and an inorganic salt.

For formation of such medicines, a binder, a disintegrating agent, a surface active agent, a lubricant, a flowability improver, a taste improver, a colorant, a perfume and the like can be used in addition to an excipient as mentioned above.

Specific examples of these agents are described below.

Binder

Starch, dextrin, gum arabic powder, gelatin, hydroxypropyl starch, methyl cellulose, sodium carboxymethyl cellulose, hydroxypropyl cellulose, crystalline cellulose, ethyl cellulose, polyvinylpyrrolidone and macrogol.

Disintegrating Agent

Starch, hydroxypropyl starch, sodium carboxymethyl cellulose, calcium carboxymethyl cellulose, carboxymethyl cellulose and lowly substituted hydroxypropyl cellulose.

Surface Active Agent

Sodium lauryl sulfate, soybean lecithin, sucrose fatty acid ester and Polysolvate 80.

Lubricant

Talc, waxes, hydrogenated vegetable oil, sucrose fatty acid, magnesium stearate, calcium stearate, aluminum stearate and polyethylene glycol.

Flowability Improver

Light silicic anhydride, dry aluminum hydroxide gel, synthetic aluminum silicate and magnesium silicate.

The compound of the formula can be used in the form of a suspension, an emulsion, a syrup or an elixir. Each preparation may contain a taste improver, a smell improver and a colorant.

In the case of a non-oral medicine, to obtain the intended effect, preferably the compound of the formula is applied to an adult by intravenous injection, intravenous drip, hypodermic injection or intramuscular injection, although the dose differs according to the age and body weight of a patient and the degree of the disease.

The non-oral medicine is prepared by customary procedures, and distilled water for injection, physiological saline solution, an aqueous solution of glucose, a vegetable oil for injection, sesame oil, peanut oil, soybean oil, corn oil, propylene glycol and polyethylene glycol can be used as the diluent. A fungicide, an antiseptic agent and a stabilizer can be added according to need. From the viewpoint of the stability, there is preferably adopted a method in which the non-oral medicine is filled in a vial and frozen, water is removed by the conventional freeze-drying technique, and a liquid is formed from the freeze-dried product again just before the administration. Moreover, an isotonic agent, a stabilizer, an antiseptic agent, an analgesic agent or the like can be added.

As other non-oral medicines, there can be mentioned ointments such as a lotion for external application and an unguent, and a suppository for application to the rectum, and these are prepared by customary procedures.

EXAMPLE 1

| (1) Corn starch | 44 g |
| --- | --- |

| -continued | |
|---|---|
| (2) Crystalline cellulose | 40 g |
| (3) Calcium carboxymethyl cellulose | 5 g |
| (4) Light silicic anhydride | 0.5 g |
| (5) Magnesium stearate | 0.5 g |
| (6) Compound of formula | 10 g |

According to the above-mentioned recipe, components (1) through (6) were mixed, and the mixture was compression molded by a tableting machine to obtain tablets, each having a weight of 200 mg.

Each tablet contained 20 mg of the compound of the formula, and 5 to 25 tablets were divided and administered several times per day to an adult.

EXAMPLE 2

| (1) Crystalline cellulose | 84.5 g |
|---|---|
| (2) Magnesium stearate | 0.5 g |
| (3) Calcium carboxymethyl cellulose | 5 g |
| (4) Compound of formula | 10 g |

According to the above-mentioned recipe, components (1) and (4) and a part of component (2) were homogeneously mixed, compression-molded and pulverized, and component (3) and the remainder of component (2) were added to the pulverized product and the mixture was compression-molded by a tableting machine to obtain tablets, each having a weight of 200 mg.

Each tablet contained 20 mg of the compound of the formula, and 5 to 25 tablets were divided and administered several times per day to an adult.

EXAMPLE 3

| (1) Crystalline cellulose | 34.5 g |
|---|---|
| (2) 10% Ethanol solution of hydroxypropyl cellulose | 50 g |
| (3) Calcium carboxymethyl cellulose | 5 g |
| (4) Magnesium stearate | 0.5 g |
| (5) Compound of formula | 10 g |

According to the above-mentioned recipe, components (1), (2), and (5) were homogeneously mixed, kneaded according to customary procedures, granulated by a granulating machine, dried and pulverized, and components (3) and (4) were mixed into the pulverized product and the mixture was compression-molded by a tableting machine to obtain tablets, each having a weight of 200 mg.

Each tablet contained 20 mg of compound of the formula, and 5 to 25 tablets were divided and administered several times per day to an adult.

EXAMPLE 4

| (1) Corn starch | 84 g |
|---|---|
| (2) Magnesium stearate | 0.5 g |
| (3) Calcium carboxymethyl cellulose | 5 g |
| (4) Light silicic anhydride | 0.5 g |
| (5) Compound of formula | 10 g |

According to the above-mentioned recipe, components (1) through (5) were homogeneously mixed, and the mixture was compression-molded by a compression molding machine, pulverized by a pulverizing machine and classified to obtain a granule.

Each gram of the granule contained 100 mg of the compound of the formula, and 0.5 to 5 g of the granule was divided and administered several times per day to an adult.

EXAMPLE 5

| (1) Crystalline cellulose | 55 g |
|---|---|
| (2) 10% Ethanol solution of hydroxypropyl cellulose | 35 g |
| (3) Compound of formula | 10 g |

According to the above-mentioned recipe, components (1) through (3) are mixed and kneaded according to customary procedures, granulated by a granulating machine, dried and classified to obtain a granule.

Each gram of the granule contained 100 mg of the compound of the formula, and 0.5 to 5 g of the granule of the formula was divided and administered several times per day to an adult.

EXAMPLE 6

| (1) Corn starch | 89.5 g |
|---|---|
| (2) Light silicic anhydride | 0.5 g |
| (3) Compound of formula | 10 g |

According to the above-mentioned recipe, components (1) through (3) were homogeneously mixed and 200 mg of the mixture was filled into capsule No. 2.

Each capsule contained 20 mg of the compound of the formula, and 5 to 25 capsules were divided and administered several times per day to an adult.

EXAMPLE 7

| (1) Soybean oil | 5 g |
|---|---|
| (2) Distilled water for injection | 89.5 g |
| (3) Soybean phospholipid | 2.5 g |
| (4) Glycerol | 2 g |
| (5) Compound of formula | 1 g |

According to the above-mentioned recipe, component (5) was dissolved in components (1) and (3), and the solution was emulsified by addition of a solution of components (2) and (4) to obtain an injection.

What is claimed is:

1. A brain function-improving medicine comprising, as an active ingredient, in an effective amount, a compound represented by the following formula:

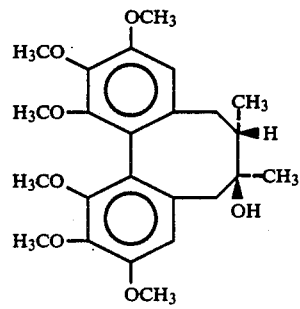

in a pharmaceutically acceptable carrier.

2. A brain function-improving medicine comprising an effective amount to improve brain function of the compound in claim 1 which is in the form of an oral medicine selected from the group consisting of a tablet, a capsule, a granule, a fine granule and a powder or a non-oral medicine selected from the group consisting of an injection and a suppository.

3. A method for treating a disease caused by reduction of the central acetylcholinergic function, said method comprising the steps of administering to a mammalian organism in need of such treatment an effective amount to improve the disease caused by reduction of the central acetylcholinergic function of a compound represented by the following formula:

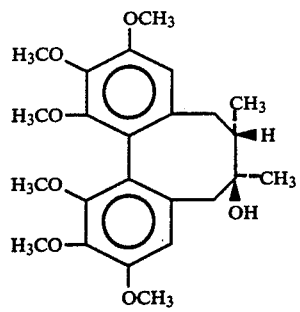

4. A method according to claim 3, wherein the compound is applied at a daily dose of 5 to 500 mg to an adult.

5. A method according to claim 3, wherein said disease caused by reduction of the central acetyl cholinergic function is Alzheimer's disease, Alzheimer type senile dementia, Huntington's chorea or Pick's disease.

* * * * *